United States Patent [19]

Kokusho et al.

[11] Patent Number: 4,782,019

[45] Date of Patent: Nov. 1, 1988

[54] ENZYMATIC PRODUCTION OF SPHINGOPHOSPHOLIPID DERIVATIVES

[75] Inventors: Yoshitaka Kokusho, Kunitachi; Shigeaki Kato; Haruo Machida, both of Hino, all of Japan

[73] Assignee: Meito Sangyo Kabushiki Kaisha, Aichi, Japan

[21] Appl. No.: 598,696

[22] Filed: Apr. 10, 1984

[30] Foreign Application Priority Data

Apr. 11, 1983 [JP]  Japan ................................ 58-63307

[51] Int. Cl.⁴ ...................... C12P 19/30; C12P 19/32; C12P 9/00; C12P 17/00
[52] U.S. Cl. ...................................... 435/89; 435/92; 435/68; 435/52; 435/106; 435/113; 435/115; 435/120; 435/121; 435/122; 435/125; 435/127; 435/128; 435/118; 435/131; 435/117
[58] Field of Search ............... 435/128, 195, 196, 198, 435/74, 87, 88, 89, 72, 74, 85, 92, 68, 106, 113, 115, 120-128, 118, 131

[56] References Cited

FOREIGN PATENT DOCUMENTS 1581810 4/1978 United Kingdom .

OTHER PUBLICATIONS

Fauvel, J. et al., Studies on Glycerophospholipids, Biochim. Biophys. Acta, vol. 792, pp. 72–78, Jan. 17, 1984.
R. M. C. Dawson, "The Formation of Phosphatidylglycerol and Other Phospholipids by the Transferase Activity of Phospholipase D, J. Biochem., 102, (1967), pp. 205–210.
F. M. Davidson & C. Long "The Structure of the Naturally Occurring Phosphoglycerides, J. Biochm., vol. 69, (1958), pp. 458–466.
Y. Okawa & T. Yamaguchi, "Studies on Phospholipases from Streptomyces", J. Biochem., vol. 78, (1975) pp. 363–372.
S. F. Yang, et al., "Transphosphatidylation by Phospholipase D, J. Biochem., vol. 242, (1967), pp. 477–484.

*Primary Examiner*—Blondel Hazel
*Attorney, Agent, or Firm*—Sherman and Shalloway

[57] ABSTRACT

A process for producing a sphingophospholipid derivative comprising reacting a sphingophospholipid with a specified compound having an alcoholic hydroxyl group selected from the group consisting of specified primary alcohol compounds, specified secondary alcohol compounds and specified saccharides or their phenol glycosides in the presence of phospholipase DM.

3 Claims, No Drawings

ENZYMATIC PRODUCTION OF SPHINGOPHOSPHOLIPID DERIVATIVES

This invention relates to a sphingophospholipid derivative derived from a sphingophospholipid and a compound having an alcoholic hydroxyl group by an enzymatic technique, and a process for production thereof.

The process of this invention can produce a broad range of sphingophospholipid derivatives including primary alcohol derivatives, secondary alcohol derivatives and saccharide derivatives of sphingophospholipids which have not been known heretofore to be producible by an enzymatic technique.

Particularly, this invention relates to a process for producing a sphingophospholipid derivative, which comprises reacting a sphingophospholipid with a broad range of primary alcohols including those which have been considered incapable of giving sphingophospholipid derivatives by an enzymatic technique, or a secondary alcohol, or a saccharide or its phenol glycoside which has been unable to give a sphingophospholipid derivative by an enzymatic technique, in the presence of phospholipase DM having an optimum temperature of 60° to 70° C. and an optimum pH of about 7 which differs from cabbage-derived phospholipase D (optimum temperature not more than 40° C. optimum pH 5.4–5.6) whicn has heretofore been used in the enzymatic procss of other phospholipids.

The term "sphingophospholipid derivative", as used in the present application, denotes a new sphingophospholipid different from the starting sphingophospholipid, which is obtained by hydrolyzing the ester linkage between the phosphoric acid structural moiety and the alcohol structural moiety of the starting sphingophospholipid and simultaneously transferring the N-aryl sphingosine-1-phosphoric acid structural moiety to the aforesaid compound having an alcoholic hydroxyl group.

More specifically, this invention relates to a process for producing a sphingophospholipid derivative represented by the following formula (I)

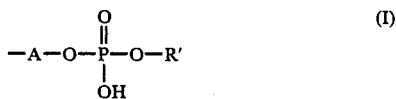

wherein A and R' are as defined below, which comprises reacting a sphingophospholipid represented by the following formula (II)

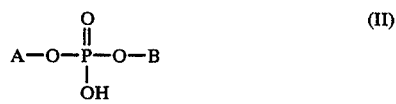

wherein A is a moiety represented by the following formula (i)

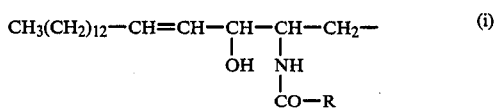

or the following formula (ii)

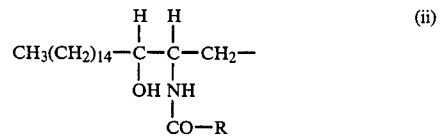

in which R represents a saturated or unsaturated aliphatic hydrocarbon group having 16 to 24 carbon atoms, and B represents $-(CH_2)_2{}^+N(CH_3)_3$ $-(CH_2)_2NH_2$ or $-CH_2CH(OH)CH_2(OH)$.

with a compound having an alcoholic hydroxyl group selected from the group consisting of (1) primary alcohol compounds having a primary alcoholic hydroxyl group and a $C_1$-$C_{20}$ saturated or unsaturated aliphatic or aromatic hydrocarbon group R' which may be substituted by a substituent selected from the class consisting of halogen, amino, carboxyl and hydroxyl; primary alcohol compounds having a primary alcoholic hydroxyl group and a residue R' of a $C_1$-$C_{20}$ saturated or unsaturated aliphatic or aromatic hydrocarbon containing in the molecule a linkage selected from the group consisting of ether, ester and amide linkages; and heterocyclic primary alcohol compounds having a primary alcoholic hydroxyl group and a heterocyclic residue R' selected from the group consisting of pyridoxine, cytidine, arabinocytidine and adenosine;

(2) secondary alcohol compounds having a secondary alcoholic hydroxyl group and a $C_3$-$C_8$ aliphatic hydrocarbon group R' which may be substituted by a substituent selected from the class consisting of halogen, amino, mono- or di-alkylamino of not more than 3 carbon atoms, and phenyl; and secondary alcohol compounds having a secondary alcoholic hydroxyl group and a $C_4$-$C_6$ alicyclic hydrocarbon group R'; and (3) saccharides selected from the group consisting of pentoses having a pentose residue R' and a primary alcoholic hydroxyl group and hexoses having a hexose residue R' and a primary alcoholic hydroxyl group, in which the pentose residue R' or the hexose residue R' may be substituteed by amino or acetylamino; and phenol glycosides of said saccharides;

in the presence of phospholipase DM; and to the sphingophospholipid derivative so obtained.

It has previously been known that phospholipase D catalyzes a reaction of hydrolyzing the choline base-phosphoric acid ester of a sphingophospholipid such as sphingomyelin to form choline and N-acylsphingosine-1-phosphoric acid [F. M. Davidson, "Biochem. J., vol. 69, 458–466 (1958)" (cabbage phospholipase D); and Y. Okawa et al., "J. Biochem., 78, 363–372 (1975)" (phospholipase D produced by Streptomyces hachijoensis)].

It was reported that when a glycerophospholipid such as lecithin is reacted with ethanol in the presence of phospholipase D, the ester linkage between the N-aryl-sphingosine-1-phosphosphoric structural moiety and the alcohol structural moiety of the phospholipid is hydrolyzed, and simultaneously, by the action of the enzyme to transfer the phosphatidyl group, phosphatidyl ethanol is formed [R. M. C. Dawson: Biochem. J., 102, 205 (1967); and S. F. Yang: J. Biol. Chem., 242, 477 (1967)].

It has not been known however that when a sphingophospholipid is subjected to the action of phospholipase DM in the presence of the compound having an alcoholic hydroxyl group shown in (1) to (3) above, the ester linkage between the phosphoric acid structural moiety and the alcohol structural moiety of the sphingophospholipid is hydrolyzed, and simultaneously, by the action of the enzyme to transfer N-acylsphingosine-1-phosphoric acid, a new sphingophospholipid derivative different from the starting sphingophospholipid is formed.

The present inventors already discovered the existence of microorganisms having the ability to produce phospholipase D which differ from the known cabbage-derived phospholipase D in optimum temperature, optimum pH, etc., and disclosed them in Japanese Patent Application No. 161076/1981 (Laid-Open Patent Publication No. 63388/1983 laid open on April 15, 1983), and Japanese Patent Application No. 163475/1981 (Laid-Open Patent Publication No. 67183/1983 laid open on April 21, 1983).

Further investigations have led to the surprising discovery that the enzyme (to be called phospholipase DM herein) produced by the aforesaid phospholipase D-producing microrganisms shows an enzymatic catalytic action when it is caused to act on sphingophospholipid in the presence of a compound having an alcoholic hydroxyl group including primary alcohol compounds, secondary alcohol compounds, saccharides and their phenol glycosides, whereby simultaneously with hydrolysis, a transfer reaction between it and the compound having an alcoholic hydroxyl group selected from the groups (1), (2) and (3) becomes possible by the action of the enzyme to transfer N-acylsphingosine-1-phosphoric acid, which action has not been described in the prior literature.

This new finding has not been reported at all in the past. For example, British Patent No. 1,581,810 (corresponding to West German OLS No. 2717547) proposes a process for producing a phospholipid by utilizing the action of the cabbage-derived phospholipase to transfer the phosphatidyl group. The patent, however, neither describes nor suggests the action of the enzyme to transfer N-acylsphingosine-1-phosphoric acid. This patent document only discloses a primary alcohol transfer reaction between a glycerophospholipid represented by the general formula given there and a primary alcohol having a linear or branched alkyl group having up to 5 carbon atoms and being optionally substituted by hydroxyl, halogen, amino or other substituents in the presence of the cabbage-derived phospholipase D. It fails to give any description about sphingophospholipids which quite differ from glycerophospholipids in the structure of a nonpolar portion.

Investigations of the present inventors have shown that there exists an enzyme newly called phospholipase DM in this invention which catalyzes the formation of a sphingophospholipid derivative from a sphingophospholipid and a primary alcohol such as geraniol ), ($C_{10}$), a seconary alcohol such as 1-amino-2-propanol ($C_3$), or a saccharide such as ribose ($C_5$); and when the sphingophospholipid of formula (II) is reacted with the compound having an alcoholic hydroxyl group selected from (1) to (3) in the presence of this phospholipase DM, the enzyme promotes the action of hydrolyzing the ester linkage between the phosphoric acid structural moiety and the alcohol structural moiety which in the prior art rarely occurs, or takes place only slowly, and by the action of enzyme to transfer N-acylsphingosine-1-phosphoric acid which has been quite unknown heretofore, new sphingophospholipid derivatives including sphingophospholipid derivatives with primary alchohols, secondary alcohols or saccharides or the glycosides thereof can be produced.

It has thus been found that new sphingophospholipids can be produced in good yields by an enzymatic method under mild conditions and by easy means without the need for complex and disadvantageous chemical synthesizing means and without a likelihood of side reactions.

It is an object of this invention therefore to provide a process for producing new sphingophospholipid derivatives by an enzymatic technique.

The above and other objects and advantages of this invention will become more apparent from the following description.

The sphingophospholipids utilized in the process of this invention are represented by the following formula (II).

$$A-O-\underset{\underset{OH}{|}}{\overset{\overset{O}{\|}}{P}}-O-B \qquad (II)$$

In formula (II), A is a moiety represented by the following formula (i)

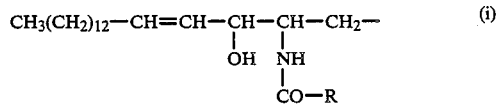

or the following formula (ii)

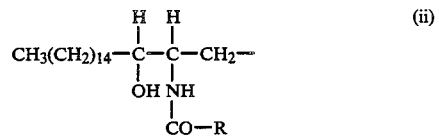

in which R represents a saturated or unsaturated aliphatic hydrocarbon group having 16 to 24 carbon atoms; and B represents $-(CH_2)_2{}^+N(CH_3)_3$, $-(CH_2)_2NH_2$ or $-CH_2CH(OH)CH_2(OH)$, The starting sphingophospholipids of formula (II) are known compounds and are available on the market, and can be extracted from naturally occurring materials, or synthesized, by methods known per se. For example, sphingomyelin, ceramidephosphoryl ethanolamine, and ceramidephosphoryl glycerol, which are extracted from the tissues of animals, plants or microorganisms by known means, may be used singly or in combination either as such or after purification. Or the structures of these may be partly or wholly synthesized chemically by known methods.

In the process of this invention, the compound having an alcoholic hydroxyl group which is to be reacted with the starting sphingophospholipids of formula (II) is selected from the groups (1) to (3) below.

(1) Primary alcohol compounds having a primary alcoholic hydroxyl group and a $C_1$-$C_{20}$ saturated or unsaturated aliphatic or aromatic hydrocarbon group R′ which may be substituted by a substituent selected from the class consisting of halogen, amino, carboxyl and hydroxyl; primary alcohol compounds having a primary alcoholic hydroxyl group and a residue R′ of a $C_1$-$C_{20}$ saturated or unsaturated aliphatic or aromatic hydrocarbon containing in the molecule a linkage selected from the group consisting of ether, ester and amide linkages; and heterocyclic primary alcohol compounds having a primary alcoholic hydroxyl group and a heterocyclic residue R' selected from the group consisting of pyridoxine, cytidine, arabinocytidine and adenosine.

(2) Secondary alcohol compounds having a secondary alcoholic hydroxyl group and a $C_3$–$C_8$ aliphatic hydrocarbon group R' which may be substituted by a substituent selected from the class consisting of halogen, amino, mono- or di-alkylamino of not more than 3 carbon atoms, and phenyl; and secondary alcohol compounds having a secondary alcoholic hydroxyl group and a $C_4$–$C_6$ alicyclic hydrocarbon group R'.

(3) Saccharides selected from the group consisting of pentoses having a pentose residue R' and a primary alcoholic hydroxyl group and hexoses having a hexose residue R' and a primary alcoholic hydroxyl group, in which the pentose residue R' or the hexose residue R' may be substituted by amino or acetylamino; and phenol glycosides of said saccharides.

Examples of the primary alcohols belonging to group (1) include aliphatic alcohols such as methanol, ethanol, 1-propanol, 1-butanol, 1-pentanol, isoamyl alcohol, 1-hexanol, 1-heptanol, 1-octanol, 1-nonanol, 1-decanol, 1-undecanol, 1-dodecanol, 1-hexadecanol, geraniol, citronellol, farnesol, phytol, ethylene glycol, 1,2- propanediol, 1,3-propanediol, glycerol, 1,4-butanediol, 1,6-hexanediol, 2-n-butyl-1,3-propanediol, 2-ethyl-1,3-hexanediol, 2-chloroethanol, ethanolamine, 3-amino-1-propanol, diethanolamine, triethanolamine, 6-amino-1-hexanol, pantothenyl alcohol, pantetheine, serine, serine ethyl ester, monolaurin, 2-hydroxyethyl methacrylate, triethylene glycol, diethylene glycol monobutyl ether, N-oleoyl ethanolamine, N-stearoyl ethanolamine, N-lauroyl ethanolamine, N,N-dibutyl ethanolamine, N,N,N-trimethylpropanolamine, N,N,N-trimethylbutanolamine, tetraethylene glycol, hexaethylene glycol, and octaethylene glycol; aromatic alcohols such as benzyl alcohol, beta-phenethyl alcohol, 3-phenyl-1-propanol, cinnamyl alcohol, p-chlorobenzyl alcohol, p-aminophenethyl alcohol, beta-hydroxyethylaniline, and anisic alcohols; and heterocyclic compounds such as 2-(3-indole)ethanol, pyridoxine, pyridoxal, 5-hydroxymethylcytosine, cytidine, uridine, adenosine, guanosine, arabinocytidine and thiamine.

Specific examples of the secondary alcohols belonging to group (2) include 2-propanol, 2-butanol, 2-pentanol, 2-hexanol, 2-heptanol, 2-octanol, 1-chloro-2-propanol, 1-amino-2-propanol, diisopropanolamine, 1-phenylethanol, 1-phenyl-2-propanol, cyclobutanol, and cyclohexanol.

Specific examples of the saccharides of group (3) include D- and L-arabinoses, 2-deoxy-D-ribose, D-ribose, D-lyxose, D-xylose, 2-deoxy-D-glucose, D-glucose, D-mannose, D-galacose, D-fructose, L-sorbose, D-glucosamine, D-mannosamine, D-galactosamine, N-acetyl-D-glucosamine, N-acetyl-D-galactosamine, arbutin and salicin.

Transfer of the sphingophospholipid to the saccharide by phospholipase DM occurs with saccharides having a primary alcohol group in the molecule as stated above, but not with saccharides having no primary alcohol group with reduction of the 6-position such as fucose and rhamnose. Sphingophospholipid derivatives from ribose, arabinose and fructose show a single spot when separated by TLC. Furthermore, when glucose is treated with triphenylchloromethane in a pyridine solution to substitute the primary alcohll group of glucose by triphenylmethane, the aforesaid transfer does not take place. From the foregoing facts, it is presumed that the transfer of the sphingophospholipid to the saccharide by phospholipase DM occurs at the site of the primary alcohol group of the saccharide.

The compounds having an alcoholic hydroxyl group belonging to groups (1) to (3) may be natural or synthetic materials. Preferably, they are used after purification by suitable means to avoid inclusion of other compounds having an alcoholic hydroxyl group. Examples of the purification means includ distillation, recrystallization, column chromatography on alumina, silica gel, activated carbon and ion exchange resins, and thin-layer chromatography, and suitable combinations of these.

According to the process of this invention, the sphingophospholipid of formula (II) is reacted with the compound having an alcoholic hydroxyl group selected from the groups (1) to (3) in the presence of phospholipase DM.

The phospholipase DM utilized at this time may, for example, be those phospholipases DM produced by phospholipase DM-producing microorganisms, which can be distinguished from the known phospholipase D extracted from cabbage (optimum temperature not more than 40° C., optimum pH 5.4–5.6) in that they have an optimum temperature in the range of 60° to 70° C. and an optimum pH of about 7. All phospholipases DM having the action of transferring N-acylsphingosine-1-phosphoric acid can be utilized irrespective of their origin.

The phospholipases DM can be distinguished from the known phospholipase D in that they catalyze formation of a sphingophospholipid derivative from the sphingophospholipid of formula (II) and geraniol as a $C_{10}$ primary alcohol, 2-butanol as a $C_4$ secondary alcohol, or ribose as a $C_5$ saccharide.

Examples of the phospholipase DM-producing microorganisms are those belonging to the genus Nocardiopsis, such as Nocardiopsis sp. No. 779 (FERM-P No. 6133; international deposit number BP 512 under the Budapest Treaty), disclosed in the above-cited Japanese Patent Application No. 161076/1981 (Laid-Open Patent Publication No. 63388/1983 laid open on Apr. 15, 1983), and those belonging to the genus Actinomadura, such as Actinomadura sp. No. 362 (FERM-P No. 6132; international deposit number BP 511 under the Budapest Treaty) which are disclosed in Japanese Patent Publication No. 163475/1981 (Laid-Open Patent Publication No. 67183/1983 laid open on Apr. 21, 1983). Table 1 below summarizes the differences in enzymological properties between the phospholipases DM used in the process of this invention and the known phospholipase D.

TABLE 1

|  | Phospholipase DM from the Actinomadura strain | Phospholipase DM from the Nocardiopsis strain | Known phospholipoase D from cabbage |
| --- | --- | --- | --- |
| Optimum temperature (°C.) | 60–70 | 60–70 | below 40 |

TABLE 1-continued

|  | Phospholipase DM from the Actinomadura strain | Phospholipase DM from the Nocardiopsis strain | Known phospholipoase D from cabbage |
| --- | --- | --- | --- |
| Optimum pH | About 7 | About 7 | 5.4–5.6 |
| Activators | Nonionic surfactants such as Triton X-100, deoxycholic acid Cholic acid, $Ca^{++}$, diethyl ether, and albumin | Nonionic surfactants such as Triton X-100, diethyl ether, and $Ca^{++}$ | Anionic surfactants such as sodium dodecylsulfate, deoxycholic acid, phosphatidic acid, $Ca^{++}$, diethyl ether |
| Inhibitors | Cetyl pyridinium chloride | Sodium dodecylsulfate, and cetyl pyridinium chloride | EDTA, cationic surfactants, choline, ethanolamine, and p-chloromercury benzoate |
| N—acylsphingosine-1-phosphoric acid transferase activity | Primary aliphatic, aromatic and heterocyclic alcohols ($C_{1-20}$); secondary alcohols having $C_3$–$C_8$ aliphatic hydrocarbon group or $C_4$–$C_6$ alicyclic hydrocarbon groups; saccharide such as pentose and hexose | Primary aliphatic, aromatic and heterocyclic alcohols ($C_{1-20}$); secondary alcohols having $C_3$–$C_8$ aliphatic hydrocarbon group or $C_4$–$C_6$ alicyclic hydrocarbon groups; saccharide such as pentose and hexose | Primary aliphatic, aromatic and heterocyclic alcohols ($C_{1-20}$); secondary alcohols having $C_3$–$C_8$ aliphatic hydrocarbon group or $C_4$–$C_6$ alicyclic hydrocarbon groups; saccharide such as pentose and hexose |
| Catalytic action on the formation of sphingophospholipid derivative between the alcoholic compound and sphingomyelin | Geraniol ($C_{10}$), 2-butanol ($C_4$), ribose ($C_5$) Yes | Geraniol ($C_{10}$), 2-butanol ($C_4$), ribose ($C_5$) Yes | Geraniol ($C_{10}$), 2-butanol ($C_4$), ribose ($C_5$) No |

Presumably, it is due to the aforesaid differences in enzymological properties between the known phospholipase D and the phospholipases DM used in the process of this invention that sphingophospholipid derivatives which cannot be obtained by using the known phospholipase D can be produced by the process of this invention. It should be understood however that this presumption does not in any way limit the process of this invention.

The microbiological properties of Nocardiopsis sp. No. 779 (FERM-P No. 6133; BP 512) and Actinomadura sp. No. 362 (FERM-P No. 6132; BP 511) which have the ability to produce phospholipase DM and can be utilized in the process of this invention, the method of measuring the potencies of the phospholipases DM produced by these microorganism strains and their physico-chemical properties are described below.

Microbiological properties of Nocardiopsis sp. No. 779 (FERM-P No. 6133; BP 512):-

(a) Morphology

Growth good on glucose-asparagine-agar, glycerolasparagine-agar, and yeast-malt-agar media, and moderate in a starch-inorganic salt-agar medium, forming colonies of aerial mycelia.

The color of the colonies having spores formed therein changes slightly with the type of the culture medium and the time of observation, but is generally white to grayish white to bright gray.

Aerial mycelia do not form, or grow poorly, on sucrose-nitrate-agar, nutrient agar and oatmeal-agar media.

Microscopic observation of this strain grown on an agar medium shows that the aerial hyphae are 0.5 to 0.8 micron in diameter and are long and straight with many branches, and sometimes gently wavy or flexuous. The entire aerial mycelia are formed of chains all composed of about 10 to 100 or more spores.

The spores are 0.5–0.8×0.5×1.6 micron long, and nearly of a short cylindrical shape, and their sizes are slightly irregular.

Substrate hyphae are 0.4 to 0.7 micron in diameter, and stretch with branches. They do not always fragment on an agar medium, but when cultivated in a liquid culture medium, they fragment into small fragments in almost all cases.

Flagellated spores, sporangia, sclerotia, etc., are not formed, however.

(b) Characteristics on various media

The following experiments were carried out mainly in accordance with the methods of E. B. Shirling (Int. J. Syst. Bacteriol., vol. 16, pages 313–340, 1966).

The colors of the mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after the lapse of one week from the initiation of cultivation which was before the formation of spores. No result is given where the evaluation of colors on the surfaces of substrate mycelia was difficult because of the early formation of spores.

Sucrose-nitrate-agar medium

Growth: Thin and poor. Colorless.
Color of substrate mycelium: Grayish white (19).
Aerial mycelium: Slightly formed. Colorless.
Soluble pigment: None.
  Glucose-asparagine-agar medium
Growth: Good. Yellowish white (Y-1-19).

Color of substrate mycelium: Yellowish gray (rY-2-19).
Aerial mycelium: Abundant in cottony form. Light brownish gray (rO-1-17).
Soluble pigment: None.

Glycerol-asparagine-agar medium

Growth: Good.
Color of substrate mycelium: Pale yellow (rY-3-19).
Aerial mycelium: Formed thinly in cottony form. Light gray (18).
Soluble pigment: None.

Starch-inorganic salt-agar medium

Growth: Good. Yellowish gray (Y-1-19).
Color of substrate mycelium: Yellowish gray (rY-1-19).
Aerial mycelium: Moderate, powdery. Grayish white (19).
Soluble pigment: None.

Tyrosine-agar medium

Growth: Good. Yellowish brown (YO-3-16).
Color of substrate mycelium: Light brown (0-3-15).
Aerial mycelium: Good to excellent. Light gray (18).
Soluble pigment: Brown melanoid pigment produced.

Nutrient agar medium

Growth: Poor. Colorless.
Color of substrate mycelium: Brownish white (YO-1-19).
Aerial mycelium: Not formed.
Soluble pigment: None.

Yeast-malt-agar medium

Growth: Good.
Color of substrate mycelium: Dull yellow orange (YO-4-18).
Aerial mycelium: Good to excellent. Grayish white (19).
Soluble pigment: Brown melanoid pigment produced.

Oatmeal-agar medium

Growth: Moderate. Yellowish gray (Y-1-19).
Color of substrate mycelium: Yellowish gray (Y-1-19).
Aerial mycelium: Poor. White (20).
Soluble pigment: None.

(c) Physiological properties
1. Growth temperature
Grows at about 5° to 30° C., and best at 20° to 30° C.
2. Liquefaction of gelatin
Negative (when cultivated on a glucose-peptonegelatin medium at 25° C. for 3 weeks).
3. Hydrolysis of starch
Positive (when cultivated on a starch-agar medium at 25° C. for 3 to 4 weeks).
4. Coagulation and peptonization of skimmed milk
Both negative (when cultivated at 30° C. for 3 to to 4 weeks).
5. Formation of a melanoid pigment
Positive on peptone-yeast-iron-agar and tyrosine-agar media (at 25° C. for 2 to 4 days).
(d) Utilization of carbon sources (when cultivated at 30° C. for 10 to 16 days)
L-arabinose: —
Sucrose: —
D-xylose: —
 Inositol: —
 D-glucose: +
 L-rhamnose: —
D-fructose: —
Raffinose: —
(e) Chemical analysis of cells
2,6-Diaminopimelic acid of this strain has the meso-form of DAP in hydrolysates of whole organisms, and does not contain hydroxydiaminopimelic acid. The sugar pattern of the cell walls of this strain is such that it lacks arabinose, xylose, madurose, rhamnose, but contains galactose and mannose. The present strain does not contain nocardomycolic acid.

The foregoing analytical results are evaluated in accordance with the classification methods described in Bergey's Manual of the Determinative Bacteriology, 8th edition, pages 657–658 (1974), M. P. Lechevalier and H. A. Lechevalier, "Inter. J. System. Bacteriol.", vol. 20, pages 435–443, 1970, and J. Meyer, Int. J. Syst. Bacteriol., vol. 26, pages 487–493, 1976. It was found that the cell wall type of the present strain is type III, and its cell wall sugar pattern is type C.

Because the present strain has cell wall type III and cell wall sugar pattern C, the Lechevalier's classification method shows it to belong to either of the genera Geodermatophilus, Actinobifida, Thermoactinomyces and Actinomadura of the dassonvillei type.

Since, however, the present strain has such morphological characteristics that all of the aerial mycelia are composed of long chains of spores, the substrate mycelia are finely fragmented, but no endospores, flagellated spores nor sporangia are found in it, it is reasonable to identify this strain as belonging to the genus Actimomadura of the dassonvilleic type. It is noted in this regard that the genus Actinomadura of the dassonvillei type has recently been unified into the new genus Nocardiopsis advocated by J. Meyer, and is generally dealt with by the name of genus Nocardiopsis.

Thus, the present strain was named Nocardiopsis sp. No. 779. It was deposited in Fermentation Research Institute of the Agency of Industrial Science and Technology, Japan under the deposit number "FERM-P No. 6133 (the international deposit number BP 512)".

In the present invention, not only Nocardiopsis sp. No. 779 and its mutant strains, but also all other strains belonging to the genus Nocardiopsis (the former genus Actinomadura of the dassonvillei type) and capable of producing phospholipase DM can be used to produce phospholipase DM.

Microbiological properties of Actinomadura sp. No. 362 (FERM-P No. 6132; the international deposit number BP 511): -

(a) Morphology
Growth good on starch-inorganic salt-agar, tyrosine-agar, yeast-malt-agar, and oatmeal-agar media, but moderate on a glycerol-asparagine-agar medium, forming colonies of aerial mycelia.

The color of the colonies having spores formed therein varies slightly with the type of the culture medium and the time of observation, but generally it is slightly purplish grayish white to gray.

Aerial hyphae are not formed, or formed only poorly, on sucrose-nitrate-agar, nutrient agar and glucose-asparagine-agar media.

Microscopic observation of the present strain grown on an agar medium shows that the aerial myceia are branched with a width of 0.7 to 0.8 microns, partly form loops or helical filaments, and are mainly straight with some flexuous parts, and their tips are mostly wound in loop form.

Spores are formed in 10 to 100 or more chains, and constitute almost the entire aerial mycelia.

The size of the spores is 0.7–0.8×0.7×1.6 microns, and their shape is short-cylindrical. Both their size and shape are slightly irregular.

The substrate mycelia are 0.4 to 0.7 micron wide, and stretch flexuously with irregular branches. No flagellated spores, sporangia nor sclerotia are formed.

Fragmentation of the septa and mycelia is not observed. (But sometimes, fragmentation of the mycelia occurs in liquid culture.)

(b) Characteristics on various culture media

The following experiments were carried out mainly in accordance with the methods of E. B. Shirling (Int. J. Syst. Bacteriol., vol. 16, pages 313–340, 1066).

The colors of mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after one week from the initiation of cultivation which was before the formation of spores. No result is given where the evaluation of colors on the surfaces of substrate mycelia was difficult because of the early formation of spores.

Sucrose-nitrate-agar medium

Growth: Poor. Grayish white (19).
Color of substrate mycelium: Grayish white (19).
Aerial mycelium: Formed moderately in powder form. Grayish white (19).
Soluble pigment: None.

Glucose-asparagine-agar medium

Growth: Good. Yellowish white (Y-1-19).
Color of substrate mycelium: Light olive gray (Y-1-18).
Aerial mycelium: Formed poorly. Light brownish gray (YO-1-19).
Soluble pigment: None.

Glycerol-asparagine-agar medium

Growth: Moderate. Greenish white (gY-1-19).
Color of substrate mycelium: Pale yellowish brown (rY-2-18).
Aerial mycelium: Formed thickly in powder form. Light gray (18).
Soluble pigment: None.

Starch-inorganic salt-agar medium

Growth: Good. Yellowish gray (Y-1-19).
Color of substrate mycelium: Yellowish gray (Y-1-19).
Aerial mycelium: Good. Pale orange (O-2-19).
Soluble pigment: None.

Tyrosine-agar medium

Growth: Good. Pale yellowish brown (YO-2-18).
Color of substrate mycelium: Pale brown (YO-3-17).
Aerial mycelium: Good to excellent. Brownish white (O-1-19).
Soluble pigment: Brown melanoid pigment produced.

Nutrient agar medium

Growth: Thin and poor. Colorless.
Color of substrate mycelium: Brownish white (YO-1-19).
Aerial mycelium: Not formed.
Soluble pigment: Brown melanoid pigment produced.

Yeast-malt-agar medium

Growth: Good.
Color of substrate myceluim Dull yellow (rY-4-18).
Aerial mycelium: Good to excellent. Light purplish gray (pR-1-17).
Soluble pigment: None.

Oatmeal-agar medium

Growth: Good. Yellowish gray (rY-1-19).
Color of substrate mycelium: Yellowish gray (rY-1-19).
Aerial mycelium: Good to excellent. Brownish white (YO-1-19).
Soluble pigment: None.

(c) Physiological properties

1. Growth temperature

Grows at about 10° to 37° C., and best at 20° to 30° C.

2. Liquefaction of gelatin

Negative (on a glucose-peptone-gelatin medium at 25° C. for 3 weeks).

3. Hydrolysis of starch

Positive (on a starch-agar medium at 25° C. for 3 weeks).

4. Coagulation and ppptonization of skimmed milk

Not coagulated but peptonized (at 30° C. for 3 to 4 weeks).

5. Formation of a melanoid pigment

Positive on peptone-yeast-iron-agar and tyrosineagar media (at 25° C. for 2 to 4 days).

(d) Utilization of carbon sources (at 30° C. for 10 to 16 days)

L-arabinose: +
Sucrose: −
D-xylose: +
Inositol: ±
D-glucose: +
L-rhamnose: −
D-fructose: −
Raffinose: −

(e) Chemical analysis of cells 2,6-Diaminopimelic acid of this strain is of the meso-type. The sugar composition of the whole cell walls is such that it does not contain arabinose, xylose, rhamnose, but contains madurose, galactose and mannose.

The foregoing analytical results are evaluated in accordance with the classification methods described in Bergey's Manual of the Determinative Bacteriology, 8th edition, pages 657–658 (1974), and M. P. Lechevalier and H. A. Lechevalier, "Inter. J. System. Bacteriol., vol. 20, pages 435–443, 1970". It was found that the cell wall type of the present strain is type III, and its cell wall sugar pattern is type B.

Because the present strain has cell wall type III and cell wall sugar pattern B, it belongs to either of the genera Microbispora, Streptosporangium, Spirillospora, Planomonospora, Dermatophilus, and Actinomadura.

Since, however, the present strain has such morphological characteristics that spore chains composed of many spores are formed, and no sclerotia, flagellated spores nor sporangia are found in it, it is taxonomically reasonable to identify this strain as belonging to the genus Actinimomadura.

Thus, the present strain was named Actinomadura sp. No. 362. It was deposited in Fermentation Research Institute of the Agency of Industrial Science and Technology, Japan under the deposit number "FERM-P No. 6132 (the international deposit number BP 511)".

In the present invention, not only Actinomadura sp. No. 362 and its mutant strains, but also all other strains belonging to the genus Actinomadura and capable of producing phospholipase DM can be used to produce phospholipase DM.

The phospholipase DM utilized in the process of this invention is produced by cultivating the phospholipase DM-producing strain exemplified above in a culture medium, and collecting phospholipase DM from the culture broth. The cultivation can be carried out in a liquid culture or solid culture mode, but industrially, a submerged culture mode is advantageous.

Carbon sources, nitrogen sources, inorganic salts and traces of other nutrients which are generally used in microbial cultivation may be used in this invention as cultivation sources. Other nutrient sources which phospholipase DM-producing microorganisms of the genus Nocardiopsis or Actinomadura can utilize may also be used in this invention.

Examples of the carbon sources include glucose, fructose, sucrose, lactose, starch, glycerol, dextrin, molasses, sorbitol, fatty acids, oils and fats, crude lecithin, alcohols and organic acids. They may be used either singly or in combination.

The nitrogen sources may be inorganic or organic. Examples of the inorganic nitrogen souces include ammonium nitrate, ammonium sulfate, urea, sodium nitrate, ammonium phosphate monobasic, ammonium phosphate dibasic and ammonium chloride. Examples of the organic nitrogen sources include flours, brans and oil extraction residues of soybean, rice, corn, cotton seed, rape seed and wheat, corn steep liquor, peptone, yeast extract, meat extract, casein and amino acids.

Examples of the inorganic salts and trace nutrients include salts of phosphoric acid, magnesium, potassium, iron, aluminum, calcium, manganese and zinc, vitamins, nonionic surface-active agents and defoamers. Such substances promote the growth of the microorganisms or the production of phospholipane DM, and may be used as required.

The cultivation is carried out under aerobic conditions. The cultivation may be properly selected and varied within a range of temperatures at which the microorganism strain grows well and produces phospholipase DM. Temperatures of about 20° to about 35° C. are especially preferred.

The cultivation time varies depending upon the cultivating conditions. The cultivation may be performed until the amount of the phospholipase DM produced reaches a maximum. In the csse of liquid culture, for example, it is about 1 to 3 days.

The phospholipase DM produced in the culture broth is mainly dissolved in it. Hence, the phospholipase DM can be collected from the culture broth after removing solid materials from it by filtration.

In collecting the phospholipase DM from the filtrate, all methods usually employed for enzyme preparation can be utilized. The methods include, for example, salting out with ammonium sulfate, sodium chloride, etc., precipitation with organic solvents such as acetone, ethanol and methanol, dialysis, ion-exchange chromatography, adsorption chromatography, gel filtration, adsorption on adsorbents, and isoelectric precipitation. These methods may be combined if the combined use increases the effect of purifying phospholipase DM.

The phospholipase DM may be obtained in the form of a liquid or solid by, for example, adding various salts, sugars, proteins, lipids and surface-active agents as stabilizers, or by concentrating it under reduced pressure, drying it under reduced pressure or lyophilizing it without adding such stabilizers.

The enzyme activity of the phospholipase DM utilized in the process of this invention is determined by measuring the amount of a base which is formed when the phospholipase DM acts on the substrate glycerophospholipid to decompose the ester linkage between phosphoric acid and the nitrogen-containing base. Unless otherwise indicated, the activity of phospholipase DM is measured by the choline oxidase method to be described hereinafter.

Method of measuring the activity of an enzyme: -

Distilled water (0.15 ml), 0.1 ml of 0.2M TrisHCl buffer (pH 7.2) and 0.05 ml of 0.1 M aqueous calcium chloride solution are mixed with 0.1 ml of 1% emulsion of purified lecithin from egg yolk (an emulsion of 0.1 g of lecithin, 1 ml of ethyl ether and 10 ml of distilled water obtained by ultrasonication). To the mixture is added 0.1 ml of an enzyme solution and reacted at 37° C. for 20 minutes. Then, 0.2 ml of 1M Tris-HCl buffer (pH 8.0) containing 50 mM disodium ethylenediamine tetraacetate, and immediately then, the mixture is boiled for 5 minutes, followed by completely stopping the reaction. Then, 4 ml of a solution obtained by dissolving a choline colorforming agent contained in a kit of a reagent for choline esterase measurement (produced by Nippon Shoji Co., Ltd.) in a color dissolving liquid is added, and reacted at 37° C. for 20 minutes. Then, the absorbance of the reaction solution at 500 nm is measured.

As a control, the absorbance of the product obtained by the same procedure as above except that an enzyme solution previously deactivated by heat is used.

The activity of the enzyme to liberate 1 micromole of choline per minute is defined as one unit.

The physico-chemical properties of phospholipases DM produced and purified by the method shown below in section 9 (Method of purification) using Nocardiopsis sp. No. 779 and Actinomadura sp. No. 362 are described below.

1. Activity

These phospholipases DM decompose the ester linkage of phosphoric acid and a nitrogen-containing base in a glycerophospholipid to liberate the base and phosphatidic acid.

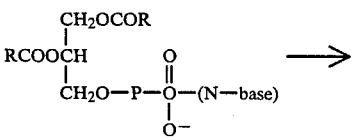

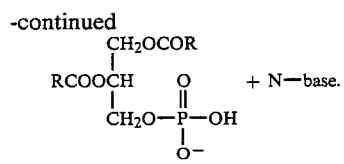

2. Substrate specificity

The same reaction as in the aforesaid method of measuring the activity of the enzyme was carried out except that 0.1 ml of an emulsion containing 0.5 micromole of each of lecithin, lysolecithin and sphingomyelin is used as a substrate and an aqueous solution containing 1% of Triton X-100 is used instead of distilled water. The amount of choline liberated as a result of the reaction is measured, and the activity of phospholipase DM on the substrate is measured. It was found that when the activity of the enzyme on lecithin is taken as 100, the relative activity of phospholipase DM derived from the Nocardiopsis strain is 4.9 on lysolecithin and 0.3 on sphingomyelin, and the relative activity of phospholipase DM derived from the Actinomadura strain is 3.6 on lysolecithin and 0.3 on sphingolyelin.

3. Optimum pH

The activity of phospholipase DM is measured by using a formic acid-sodium formate buffer at a pH of 3.0 to 4.0, an acetic acid-sodium acetate buffer at a pH of 4.0 to 5.5, a Tris-maleic acid-sodium hydroxide buffer at a pH of 5.5 to 8.5, a Tris-HCl buffer at a pH of 7.0 to 9.0, and a glycine-sodium hydroxide buffer at a pH of 9.0 to 10.0 instead of the buffer used in the method of measuring the activity of the enzyme. The optimum pH is thus measured. The optimum pH is also measured when 0.15 ml of a 1% aqueous solution of Triton X-100 (a reagent made by Wako Pure Chemicals Co., Ltd.) is used instead of 0.15 ml of distilled water.

It is found that when distilled water is used, the optimum pH of phospholipase DM from the Nocardiopsis strain is about 7 (6.5–7.0), and the optimum pH of phospholipase DM derived from the Actinomadura strain is about 7; and that when the 1% aqueous solution of Triton X-100 is used, the optimum pH of phospholipase DM derived from the Nocardiopsis strain is about 5, and the optimum pH of phospholipase DM derived from the Actinomadura strain is about 5.5.

4. Optimum temperature

The activity of the enzyme is measured by the method of measuring the activity of the enzyme at reaction temperatures of 10°, 20°, 25°, 37°, 40°, 50°, 60°, 70°, 80° and 90° C. The result is that the optimum temperature of phospholipase DM derived from the Nocardiopsis strain is 60° to 80° C., especially 60° C., to 70° C., and the optimum temperature of phospholipase DM derived from the Actinomadura strain is 55° to 80° C., especially 60° C. to 70° C.

5. pH stability

To 0.1 ml of an enzyme solution is added 0.2 ml (in the case of phospholipase DM derived from the Nocardiopsis strain) or 0.9 ml (in the case of phospholipase DM derived from the Actinomadura strain) of each of various buffers (0.1M). Specifically, there were used a glycine-HCl buffer at a pH of 3.0 to 3.5, an acetic acid-sodium acetate buffer at a pH of 3.5 to 7.0, a Tris-maleic acid-sodium hydroxide buffer at a pH of 5.0 to 8.0, a Tris-HCl buffer at a pH of 7.0 to 9.0, and a glycinesodium hydroxide buffer at a pH of 9.0 to 9.5. The mixture is maintained at 25° C. for 2 hours. Thereafter, 1.2 ml (in the case of phospholipase DM derived from the Nocardiopsis strain), or 9.0 ml (in the case of phospholipase DM derived from the Actinomadura strain) of 0.5M Tris-HCl buffer (pH 7.2) is added to the resulting enzyme buffer solution to adjust its pH to 7.0 to 7.3. The activity of the enzyme is measured by using 0.1 ml of this solution in accordance with the method of measuring the activity of the enzyme described hereinabove. The stable pH range is thus examined. It is found that phospholipase DM derived from the Nocardiopsis strain is especially stable at a pH of 4.0 to 7.0, and phospholipase DM derived from the Actinomadura strain is especially stable at a pH of 4.0 to 8.0. The stable pH range is examined by the same procedure as above except that 0.15 ml of a 1% aqueous solution of Triton X-100 is used instead of 0.15 ml of distilled water used in the method of measuring the activity of the enzyme. The results are much the same as those obtained by the aforesaid procedure.

6. Heat stability

To 0.1 ml of an enzyme solution is added 4 ml (in the case of phospholipase DM derived from the Nocardiopsis strain) or 9.9 ml (in the case of phospholipase DM derived from the Actinomadura strain) of 0.1M Tris-HCl buffer (pH 7.2), and the mixture is left to stand for 30 minutes at a temperature of 20°, 30°, 37°, 40°, 50°, 60° and 65° C. respectively. The remaining enzyme activity is then measured. It is found consequently that the activity of phospholipase DM derived from the Nocardiopsis strain is scarcely lost by heat-treatment at 30° C. for 30 minutes, and 80% of it remains after heat-treatment at 50° C. for 30 minutes and that the activity of phospholipase DM derived from the Actinomadura strain is scarcely lost by heat-treatment at 30° C. for 30 minutes, and 60% of it remains after heat-treatment at 50° C. for 30 minutes.

7. Influences of various substances

In the method of measuring the activity of the enzyme described hereinabove, 0.05 ml of an aqueous solution of each of various substances is added instead of the aqueous calcium chloride solution so that its concentration in the enzyme reaction system becomes 1 mM. The activity of the enzyme is then measured. The activity of the enzyme at the time of adding water is taken as 100, and the relative activity of the enzyme is determined. It is found that $AlCl_3$, $CuSO_4$, $ZnSO_4$, $CoCl_2$, $CaCl_2$, $FeCl_3$, $FeSO_4$, $MgCl_2$, $SnCl_2$, sodium deoxycholate, ethanol, isopropanol, t-butanol, and Triton X-100 have an activating action on phospholipase DM derivd from the Nocardiopsis strain, and $AlCl_3$, $CaCl_2$, $FeCl_3$, $FeSO_4$, $MgCl_2$, $SnCl_2$, sodium deoxycholate, ethanol, isopropanol, and t-butanol have an activating action on phospholipase DM derived from the Actinomadura strain. On the other hand, it is found that sodium dodecylsulfate and cetyl pyridinium chloride have an inhibiting action on phosphlipase DM derived from the Nocardiopsis strain, acetyl pyridinium chloride has an inhibiting action on phospholipase DM derived from Actinomadura strain.

8. Method of measuring the activity of the enzyme (As stated hereinabove)

9. Method of Purification

About 15 liters of a culture medium (pH 6.0) composed of 3.0 g of soybean flour, 1.0% of corn steep liquor, 0.5 g of peptone, 0.1% of powdery yeast extract, 1.0 g of glucose, 0.25% of $NH_4NO_3$, 0.4% of $K_2HPO_4$, 0.01% of $MgSO_4.7H_2O$, and 0.1% of Tween-85 was put in a 30 liter jar fermentor, and sterilized at 120° C. for 15 minutes. Then, 1.5 liters of a seed culture was inoculated, and cultivated at 27° C. for 40 hours.

The seed culture had been prepared by putting 100 ml of an aqueous solution (pH 6.8) containing 1% of starch, 0.25% of $(NH_4)H_2PO_4$, 0.25% of peptone, 0.2% of $K_2HPO_3$ and 0.01% of $MgSO_4.7H_2O$ in a 500 ml Sakaguchi flask, sterilizing it with steam, inoculating one platinum loopful of spores of Nocardiopsis sp. No. 779 (PB 512) or Actinomadura sp. No. 362 (BP 511) into the culture medium, and cultivating it with shaking at 30° C. for 2 days at 120 rpm.

After the cultivation, solid materials of the cells were removed by centrifugation to obtain 13 liters of a supernatant liquid (0.54 u/ml in the case of using the Nocardiopsis strain; and 1.7 u/ml in the case of using the Actinomadura strain). The supernatant liquid was cooled to 5° C., and acetone kept at −20° C. was added. By centrifugation, precipitates containing phospholipase DM corresponding to fractions having an acetone concentration of 30 to 70% were collected. The precipitates were dissolved in Tris-maleic acid buffer (pH 6.0 in the case of using the Nocardiopsis strain, and pH 6.5 in the case of using the Actinomadura strain), dialyzed against the same buffer having a molarity of 0.02M, and passed through a DEAE-cellulose column equilibrated with the same buffer. Fractions which have passed through the column were collected. A palmitoyl gauze prepared by the method of Horiuti et al. [J. Biochem. 81, 1639 (1977)] was filled in a column. After washing the column fully with water, the collected fractions were charged onto the column to adsorp active components. The column was washed with 0.05M Tris-HCl buffer (pH 7.2) and then eluted with the same buffer containing 0.2% Triton X-100. Active fractions were collected and concentrated by using an ultrafiltration membrane (Type G-10T made by Bioengineering Co., Ltd.), then charged onto a column filled with Toyo-Pearl HW-55F (made by Toyo Soda Co., Ld.) as a gel fitration carrier, and passed through it by using distilled water. Active fractions were collected and lyophilized.

The dry powder was then dissolved in 0.025M imidazole-HCl (pH 7.4) (in the case of phospholipase DM derived from the Nocardiopsis strain), or 0.025M Trisacetic acid (pH 8.3) (in the case of phospholipase DM derived from the Actinomadura strain). The solution was passed through a column filled with a polybuffer exchanger PBE$^{TN}$94 (20 ml) made by Pharmacia Fine Chemicals, Co. to adsorb active components. The column was then eluted by a pH gradient method using an eluting polybuffer made by the same company as above (pH 5.0). The eluted active fractions of phospholipase DM were collected and concentrated by an ultrafiltration membrane, and passed through a column filled with Sephadex G-75. Active fractions of phospholipase DM were collected and lyophilized.

As a result, phospholipase DM from the Nocardiopsis strain having a specific activity of 178.3 u/mg protein was recovered at an activity recovery ratio of about 40%. Furthermore, phospholipase DM from the Actinomadura strain having a specific activity of 218.3 u/mg protein was recovered at an activity recovery ratio of of about 43%.

10. Isoelectric point

Phospholipase DM derived from the Nocardiopsis strain:-
  4.85±0.1 (measured by isoelectric focusing with Ampholine)

Phospholipase DM derived from the Actinomadura strain:-
  6.4±0.1 (measured by isoelectric focusing with Ampholine)

11. Transferring action

It is known that the conventional phospholipase D produces phosphatidine from lecithin and transfers it to a linear primary alcohol having 1 to 6 carbon atoms to form an ester, but does not form such an ester with a secondry alcohol. It has been found that the enzymes (phospholipases DM) used in accordance with this invention effect transfer to not only a broad range of primary alcohols including those which it has been described cannot be transferred by the known phospholipase D, but also secondary alcohols to form esters.

The phospholiase DM used in the process of this invention reacts in accordance with the method of experimenting the transferring action (the method of determining the formation of a transfer product by TLC) to be described hereinbelow, and catalyzes the reaction of forming a sphingophospholipid derivative between a sphingophospholipid such as sphingomyelin and a primary alcohol such as geraniol ($C_{10}$), a secondary alcohol such as 2-butanol ($C_4$), or a saccharide such as ribose ($C_5$), and thus gives the alcohol compound derivative of the sphingophospholipid. The known cabbage-derived phospholipase D does not form the aforesaid derivative.

According to the process of this invention, the sphingophospholipid of formula (II) is reacted with the compound having an alcoholic hydroxyl group belonging to the groups (1) to (3) in the presence of the phospholipase DM described in detail hereinabove to give a sphingophospholipid derivative represented by the following formula (I)

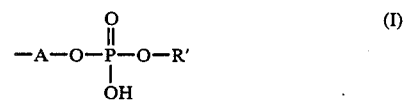

wherein A and R' are as defined hereinabove.

The phospholipase DM needs not to be a pure product, and a crude product may also be used. It may also be used after it has been immobilized to a suitable support, for example particles or films of various resins or inorganic materials such as a polypropylene film, Celite particles and glass beads.

The reaction can be carried out by contacting the sphingophospholipid of formula (II) with the alcoholic compound selected from (1) to (3) in the presence of phospholipase DM, preferably in the presence of a solvent. The solvent may be an aqueous solvent or a mixture of an aqueous solvent and an organic solvent. The alcoholic compounds (1) and (2) themselves may also serve concurrently as a solvent. Solvents containing additives which do not inhibit the enzymatic catalytic action of the phospholipase DM may also be used. For example, the solvent may contain suitable additives which serve to promote the aforesaid action or stabilize the enzyme. For example, the solvent may be an aqueous solvent containing a buffer such as acetic acid, citric acid and phosphoric acid or a neutral salt such as calcium chloride. Examples of the organic solvent are the aforesaid primary or secondary alcohols; aliphatic hydrocarbons such as n-heptane and n-hexane; alicyclic hydrocarbons such as cyclopentane, cyclohexane and cyclobutane; aromatic hydrocarbons such as benzene, toluene and xylene; ketones such as acetone and methyl isopropyl ketone; ethers such as dimethyl ether, diethyl ether and diisopropyl ether; esters such as methyl acetate and ethyl acetate; halogenated hydrocarbons such as carbon tetrachloride, chloroform and methylene chloride; amides such as dimethylformamide; and sulfoxides such as dimethyl sulfoxide.

When a mixture of the aqueous solvent and the organic solvent is used, the mixing ratio of the two can be suitably selected. For example, the ratio (V/V) of the aqueous solvent to the organic solvent may range from 50:1 to 1:10.

The mole ratio of the reactants, the amount of the phospholipase DM, and the amount of the solvent can be properly selected. For example, the alcoholic compound selected from (1) to (3) may be used in an amount of about 1 to about 1000 moles, preferably about 10 to about 1000 moles per mole of the sphingophospholipid of formula (II). The amount of the phospholipase DM may, for example, be about 10 to about 100,000 units, preferably about 100 to about 1000 units per gram of the sphingophospholipid of formula (II). The amount of the solvent may, for example, be about 10 to about 500 times the volume of the sphingophospholipid of formula (II).

The reaction proceeds at room temperature, and no cooling or heating is particularly required. If desired, the reaction may be carried out under cooling or heating, for example at a reaction temperature of about 0° C. to about 90° C., preferably about 20° to about 60° C. The reaction time can also be properly selected, and may, for example, be about 1 minute to about 10 days, preferably about 0.1 to about 72 hours, more preferably about 1 to 72 hours. As required, the reaction time may properly be changed by monitoring the proceeding of the reaction in accordance with, for example, thin-layer chromatography (TLC), and confirming the formation of the desired product.

Contacting of the sphingophospholipid of formula (II) with the alcoholic compound selected from (1) to (3) in the presence of phospholipase DM can be carried out in any desired mode, but usually under stirring or shaking conditions. When the enzyme is used in the form of an immobilized enzyme on a suitable particulate or film-like support as exemplified above, the reaction mixture may be passed through the immobilized enzyme film or the immobilized enzyme particle layer by means of a circulating pump.

The sphingophospholipid derivative formed by the above reaction may be used either directly or after it has been precipitated in the form of a salt. Or it may be isolated and purified by suitable known methods such as silica column chromatography, alumina column chromatography, high performance liquid chromatography, countercurrent distribution, gel filtration and adsorption chromatography.

According to the process of this invention, the sphingophospholipid derivative of formula (I) can be produced by reacting the sphingophospholipid of formula (II) with the alcoholic compound selected from (1) to (3) in the presence of the phospholipase DM in the manner described hereinabove.

The resulting sphingophospholipid drivatives of formula (I) have excellent surface-activating action and exert great effects on the permeability of cell membranes. Accordingly, the derivatives of formula (I) are useful as a liposome-forming substrate, or as an emulsifier for cosmetics such as cream and lotion, fat solutions for transfusion, and agricultural chemicals such as pesticides and herbicides.

Furthermore, in many cases, sphingophospholipids are known to occur in the organs, cerebrum, cell membranes, etc. of humans and have unique physiological properties. Since many of the derivatives of formula (I) obtained by the process of this invention have a similar structure to the sphingophospholipids, they are expected to exhibit various biological activities. Furthermore, by transferring to a sphingophospholipid a pharmacologically active compound containing a primary or secondary alcoholic hydroxyl group or having a primary or secondary alcoholic hydroxyl group introduced thereinto, it is possible to weaken the pharmacological side-effects of the compound, or to increase its pharmacological efficacy and reduce its dosage. Moreover, the pharmacologically active compound may be transferred to a sphingophospholipid and used as a carrier for concentrating the compound accurately on a lesion. Furthermore, it also serves as a useful protective group for a pharmacologically active compound.

The derivatives of formula (I) in accordance with this invention are also useful as intermediates for synthesis of chemicals including various medicines. For example, derivatives obtained by transferring an alcohol having halogen or amino which has high reactivity may be utilized for this purpose. A labelled sphingophospholipid derivative may be obtained by transferring a primary or secondary alcohol labelled with tritium or $^{14}C$, utilized for elucidating the metabolic pathways of sphingophospholipids.

The following examples illustrate the process of this invention in greater detail.

REFERENTIAL EXAMPLE 1

Preparation of phospholipases:-

In accordance with the Method of Purification in section (9) above, phospholipases DM were obtained in the activity recovery ratios and specific activities described in the aforesaid section using Nocardiopsis sp. No. 779 (FERM-P No. 6133; BP 512) and Actinomadura sp. No. 362 (FERM-P No. 6132: BP 512).

EXAMPLE 1 (RUNS NOS. 1 TO 55)

Sphingomyelin (derived from the bovine cerebrum; Sigma Co.) was reacted with the various alcohols shown in Table 2 below in the presence of the phospholipases DM in accordance with the method of determining the formation of transfer products by TLC. The Rf values of the products are given in Table 2.

Method of determining the formation of the transfer product by TLC:-

0.1 ml (1.2 u/0.1 ml) of an aqueous solution of the phospholipase DM was added to a reaction solution having the following formulation.

| | | |
|---|---|---|
| 1% sphingomyelin emulsion | 0.1 ml | |
| 0.4 M acetate buffer (pH 5.7) | 0.1 ml | |
| 0.1 M aqueous calcium chloride solution | 0.05 ml | |
| Distilled water | 0.05 ml | |
| 10% solution of alcohol | 0.1 ml | |

The mixture was left to stand at 37° C. for 1 to 5 hours.

The 1% sphingomyelin emulsion was prepared by adding 1 ml of diethyl ether and 10 ml of distilled water to 100 mg of sphingomyelin, and subjecting the mixture to ultrasonication for 5 minutes with ice cooling at 600 W and 20 KHz. The 10% alcohol solution was prepared by adding water or an organic solvent such as diethyl ether and acetone as required.

After standing, 0.2 ml of a 50 mM aqueous solution of EDTA (disodium ethylenediaminetetraacetate) was added, and 5 ml of a mixture of chloroform and methanol (2:1 by volume) was added. The mixture was vigorously stirred to extract the lipid (product). The resulting suspension was centrifuged for 10 minutes at 2000×g. The lower chloroform layer was separated, dried under reduced pressure at 30° C., and dissolved in 75 microliters of a mixture of chloroform and methanol (1:1 by volume) to form a sample for TLC. Ten microliters of the sample was spotted on a thin layer of silica gel (Funagel 60 Å, 20 cm×20 cm, a product of Funakoshi Yakushin K.K.), and the silica gel layer was developed with a mixture of diisobutyl ketone, acetic acid and water (40:25:5). The following reagents were used for detecting the spots. When a spot of a phospholipid other than those of the undecomposed substrate sphingomyelin and its hydrolysis product (N-acylsphingosine-1-phosphoric acid) was detected, it was determined to be the transfer product.

Detecting reagents

Color formation of phosphoric acid: Zinzade's reagent (Beise. U. J. Chromatog., 13, 104, 1964)

Color formation of primary amine: Ninhydrin reagent (a 0.25% acetone solution of ninhydrin)

Color formation of secondary amine: Hypochlorite-benzidine reagent (M. C. Bischel et al., Biohim. Biophys. Acta, 70, 598, 1963)

Color formation of purine and pyrimidine: Fluorescein-ammonia reagent (T. Wieland, et cl., Angew. Chem., 63, 511, 1951)

Color formation of saccharide: Naphthoresorcinol-phosphoric acid reagent (G. W. Hay et al., Chromatog., 11, 479, 1963)

Color formation of aminosugar: AcetylacetoneEhrlich reagent (Elson-Morgan reaction) (S. M. Partridge: Biochem. J., 42, 238, 1948).

TABLE 2

| Run No. | Alcohol added | Rf value of the transfer product |
|---|---|---|
| | Not added | |
| | Decomposition product | 0.42 |
| | substrate | 0.20 |
| 1 | Ethanol | 0.47 |
| 2 | 1-Butanol | 0.50 |
| 3 | 1-Hexanol | 0.54 |
| 4 | 1-Heptanol | 0.54 |
| 5 | 1-Octanol | 0.54 |
| 6 | 1-Decanol | 0.55 |
| 7 | 1-Dodecanol | 0.55 |

TABLE 2-continued

| Run No. | Alcohol added | Rf value of the transfer product |
|---|---|---|
| 8 | 1-Hexadecanol | 0.57 |
| 9 | Geraniol | 0.55 |
| 10 | Farnesol | 0.55 |
| 11 | Phytol | 0.57 |
| 12 | Glycerol | 0.30 |
| 13 | 1,6-Hexanediol | 0.44 |
| 14 | 2-Chloroethanol | 0.48 |
| 15 | Ethanolamine | 0.35 |
| 16 | 6-Amino-1-hexanol | 0.38 |
| 17 | Pantothenyl alcohol | 0.35 |
| 18 | Serine | 0.31 |
| 19 | Serine ethyl ester | 0.38 |
| 20 | Monolaurin | 0.50 |
| 21 | Diethylene glycol monobutyl ether | 0.50 |
| 22 | D-ribose | 0.23 |
| 23 | L-arabinose | 0.23 |
| 24 | D-glucose | 0.25 |
| 25 | 2-Deoxy-D-glucose | 0.25 |
| 26 | D-mannose | 0.24 |
| 27 | D-galactose | 0.24 |
| 28 | D-fructose | 0.25 |
| 29 | D-glucosamine | 0.25 |
| 30 | D-mannosamine | 0.25 |
| 31 | D-galactosamine | 0.25 |
| 32 | N—acetyl-D-glucosamine | 0.28 |
| 33 | N—acetyl-D-galactosamine | 0.29 |
| 34 | Salicin | 0.32 |
| 35 | Arbutin | 0.35 |
| 36 | Benzyl alcohol | 0.54 |
| 37 | beta-Phenylethyl alcohol | 0.54 |
| 38 | beta-Hydroxyethylaniline | 0.46 |
| 39 | Anisic alcohol | 0.55 |
| 40 | Pyridoxine | 0.38 |
| 41 | Cytidine | 0.28 |
| 42 | Arabinocytidine | 0.27 |
| 43 | Adenosine | 0.30 |
| 44 | Thiamine | 0.12 |
| 45 | 2-Propanol | 0.48 |
| 46 | 2-Butanol | 0.50 |
| 47 | 2-Pentanol | 0.52 |
| 48 | 2-Heptanol | 0.52 |
| 49 | 2-Octanol | 0.54 |
| 50 | 1-Chloro-2-propanol | 0.45 |
| 51 | 1-Amino-2-propanol | 0.37 |
| 52 | Diisopropanolamine | 0.38 |
| 53 | 1-Phenyl-2-propanol | 0.52 |
| 54 | Cyclobutanol | 0.50 |
| 55 | Cyclohexanol | 0.50 |

The samples were subjected to color reaction with the Zinzade's reagent to detect phospholipids. Those having special functional groups were detected by the various reagents stated hereinabove.

EXAMPLE 2 (RUNS NOS. 1 to 16)

Four hundred milligrams of sphingomyelin (derived from the bovine cerebrum; 99%; made by Sigma Co.), 1 ml of diethyl ether and 10 ml of distilled water were put in an ultrasonication cell, and with ice cooling subjected to an ultrasonication treatment for 5 minutes at 600 W and 20 KHz to form an emulsion.

Two milliliters of the sphingomyelin emulsion (80 mg of sphingomyelin), 2 ml of a 0.4M acetate buffer (pH 5.7), 1 ml of a 0.1M aqueous solution of calcium chloride and 2 ml of a 10% diethyl ether solution of geraniol were put in a test tube with a ground stopper. Then, 2 ml of an aqueous solution of phospholipase DM (8 u/ml) was added and well mixed. The mixture was left to stand at 37° C. for 5 hours. To the reaction mixture was added 0.5 ml of 0.5N hydrochloric acid, and 15 ml of a mixture of chloroform and methaol (2:1 by volume) was further added. They were vigorously mixed to extract the phospholipid. The mixture was centrifuged for 10 minutes at 2,000×g, and the lower chloroform layer was separated.

Chloroform (10 ml) was again added to the upper aqueous layer and the same extracting operation was carried out. The extracts were combined and then washed with 10 ml of 0.02N hydrochloric acid. The chloroform solution was dried under reduced pressure and the residue was dissolved in 1 ml of a mixture of n-hexane, 2-propanol and water (60:80:7).

Twenty microliters of this sample was spotted onto a thin layer of silica gel (Funagel, a product of Funakoshi Yakuhin K. K.), and the silica gel layer was developed with a solvent system composed of diisobutyl ketone, acetic acid and water (40:25:5). Three phospholipids were detected, and two of them agreed in Rf values with sphingomyelin and N-acylsphingosine-1-phosphoric acid.

The mixture of these three phospholipids was separated and purified by high-performance liquid chromatography.

The column used was a Radial-Pak cartridge silica, 8 mm×10 cm, (made by Waters Co.), and the eluent used was a mixture of n-hexane, 2-propanol and water (60:80:7). The flow rate was 2 ml/min. For detecting peaks, a 441-type ultraviolet detector (made by Waters Co.) for determining an absorption at 214 nm and a R401-type differential refractometer (made by Waters Co.) were used. The sample was injected into the column four times in an amount of 0.25 ml each time.

Three components included in the sample, i.e. geraniol, N-acylsphingosine-1-phosphoric acid and a phospholipid (presumably the transfer product), were separated by using this eluent. Then, the undecomposed sphingomyelin adsorbed on the column was eluted with n-hexane-2-propanol-water (60:80:16) as an eluent. The three phospholipids obtained were again purified by high-performance liquid chromatography by the same procedure. They were found to be a single entity by TLC and high-performance liquid chromatography.

The proportions of the three phospholipids were as follows:
N-acylsphingosine-1-phosphoric acid: about 5%
Transfer product: about 85%
Sphingomyelin: about 10%

About 60 mg of geraniol N-acylsphingosine-1-phosphate as the transfer product was obtained. The IR spectrum of this compound was measured by a liquid film method using an infrared spectrophotometer (Model A202 made by Nippon Bunko K.K.). The results are shown in Table 3 (Run No. 3).

The above procedure was repeated using the various alcohols indicated in Table 3. The IR spectra of the transfer products were measured.

In adding the alcohol to the reaction solution, it was used as a solution in water, diethyl ether of acetone depending upon the solublity of the alcohol.

The results are shown in Table 3 (Runs Nos. 1 to 2 and 4 to 16).

TABLE 3

IR spectra of transfer products between N—acylsphingosine-1-phosphoric acid and various alcohol

| Run No. | Alcohol as an acceptor | IR$\nu_{max}$ |
|---|---|---|
| 1 | Ethanol | 3300, 2930, 2860, 1640, 1545, 1465, 1380, 1230, 1085, 1035, 960, 840, 720 |
| 2 | 1-Hexadecanol | 3300, 2930, 2860, 1640, 1545, 1465, 1380, 1230, 1090, 1040, 880, 840, 720 |
| 3 | Geraniol | 3320, 2930, 2860, 1640, 1545, 1465, 1375, 1225, 1100, 1050, 1010, 880, 840, 720 |
| 4 | Ethanolamine | 3280, 2920, 2850, 1640, 1560, 1540, 1465, 1380, 1220, 1070, 1020, 960, 840, 720 |
| 5 | Glycerol | 3420, 3280, 2920, 2850, 1640, 1545, 1465, 1380, 1225, 1090, 1045, 870, 840, 720 |
| 6 | Serine ethyl ester | 3280, 2920, 2850, 1735, 1640, 1545, 1465, 1380, 1230, 1090, 1050, 960, 840, 750, 720 |
| 7 | Monolaurin | 3300, 2920, 2850, 1725, 1640, 1545, 1465, 1380, 1230, 1095, 1055, 990, 850, 720 |
| 8 | D-ribose | 3300, 2920, 2850, 1640, 1545, 1465, 1380, 1225, 1100, 1060, 1000, 860, 720 |
| 9 | D-glucosamine | 3320, 2930, 2860, 1640, 1545, 1465, 1380, 1225, 1095, 1050, 980, 855, 720 |
| 10 | Arbutin | 3300, 2920, 2850, 1640, 1545, 1500, 1465, 1380, 1225, 1100, 1060, 990, 885, 835, 720 |
| 11 | Benzylalcohol | 3320, 2920, 2850, 1640, 1545, 1500, 1465, 1380, 1230, 1100, 1070, 860, 730, 695 |
| 12 | Pyridoxine | 3300, 2920, 2850, 1640, 1545, 1465, 1380, 1220, 1090, 1055, 975, 850, 750 |
| 13 | Thiamine | 3320, 3160, 2920, 2850, 1645, 1595, 1560, 1540, 1465, 1445, 1380, 1225, 1090, 1055, 980, 910, 820, 750, 720 |
| 14 | 2-Butanol | 3300, 2920, 2850, 1640, 1545, 1465, 1380, 1230, 1095, 1045, 940, 845, 720 |
| 15 | 1-Chloro-2-butanol | 3280, 2920, 2850, 1640, 1545, 1465, 1380, 1230, 1095, 1040, 940, 835, 740, 720, 700 |
| 16 | 1-Phenyl-2-propanol | 3300, 2920, 2850, 1640, 1545, 1500, 1465, 1380, 1220, 1100, 1060, 995, 850, 740, 700 |

EXAMPLE 3 (RUNS NOS. 1 AND 2)

Glycerol N-acylsphingosine-1-phosphate (I) and ethanolamine N-acylsphingosine-1-phosphate (II) prepared in Example 1 were each emulsified in distilled water in the same way as in Example 1. One milliliter of each of the emulsions obtained (40 mg) was put in a test tube equipped with a ground stopper. Then, 1 ml of 0.4M acetate buffer, 0.5 ml of a 0.01M aqueous solution of calcium chloride, 1 ml of a 10% diethyl ether solution of geraniol and an aqueous solution of phospholipase DM (10 u/ml) were added, and well mixed. The mixture was left to stand at 37° C. for 6 hours. The same extraction and purification of the phospholipids as in Example 1 were carried out to give geraniol N-acylsphingosine-1-phosphate as a common transfer product. The amount of the product yielded was 12 mg for I and 15 mg for II. The IR spectrum of the product is shown in Table 4.

TABLE 4

| Run No. | Phospholipid | IR spectrum |
|---|---|---|
| 1 | I | 3320, 2930, 2860, 1640, 1545, 1465, 1375, 1225, 1100, 1050, 1010, 880, 840, 720. |
| 2 | II | 3320, 2930, 2860, 1640, 1545, 1465, 1375, 1225, 1100, 1050, 1010, 880, 840, 720. |

What we claim is:

1. A process for producing a sphingophospholipid derivative reprsented by the following formula (I)

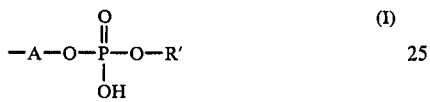

wherein A and R' are as defined below, which comprises reacting a sphingophospholipid represented by the following formula (II)

wherein A is a moiety represented by the following formula (i)

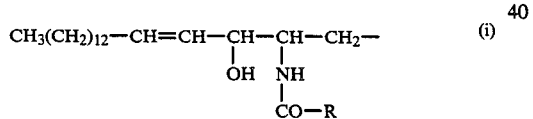

or the following formula (ii)

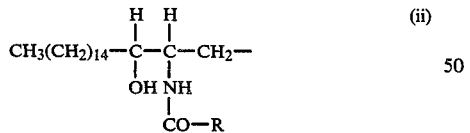

in which R represents a saturated or unsaturated aliphatic hydrocarbon group having 16 to 24 carbon atoms, and B represents $-(CH_2)_2N^+(CH_3)_3$, $-(CH_2)_2NH_2$ or $-CH_2CH(OH)CH_2(OH)$, with a compound having an alcoholic hydroxyl group selected from the group consisting of (1) alcohol compounds having a primary alcoholic hydroxyl group and a $C_1$-$C_{20}$ saturated or unsaturated aliphatic or aromatic hydrocarbon group R' which may be substituted by a substituent selected from the group consisting of halogen, amino, carboxyl and hydroxyl; alcohol compounds having a primary alcoholic hydroxyl group and a residue R' of a $C_1$-$C_{20}$ saturated or unsaturated aliphatic or aromatic hydrocarbon containing in the molecule a linkage selected from the group consisting of ether, ester and amide linkages; and heterocyclic alcohol compounds having a primary alcoholic hydroxyl group and a heterocyclic residue R' selected from the group consisting of pyridoxine, cytidine, arabinocytidine and adenosine;

(2) alcohol compounds having a secondary alcoholic hydroxyl group and a $C_3$-$C_8$ aliphatic hydrocarbon group R' which may be substituted by a substituent selected from the group consisting of halogen, amino, mono- or dialkylamino of not more than 3 carbon atoms, and phenyl; and alcohol compounds having a secondary alcoholic hydroxyl group and $C_4$-$C_6$ alicyclic hydrocarbon group R'; and (3) saccharides selected form the group consisting of pentoses having a pentose residue R' and a primary alcoholic hydroxyl group and hexoses having a hexose residue R' and primary alcoholic hydroxyl group, in which the pentose residue R' or the hexose residue R' may be substituted by amino or acetylamino; and phenol glycosides of said saccharides, in the presence of phospholipase DM, said phospholipase DM having the ability to catalyze the formation of a sphingophoispholipid-primary alcohol derivative from a sphingophospholipid and geraniol and the formation of a sphingosphospholipid-secondary alcohol derivative from a sphingopospholipid and 2-butanol, and recovering the reaction product formed.

2. The process of claim 1 wherein the sphingophospholipid of formula (II) is at least one member selected from the group consisting of sphingomyelin, ceramidephosphoryl ethanolamine, and ceramidephosphoryl glycerol.

3. The process of claim 1 wherein the reaction is carried out by contacting the sphingophospholipid of formula (II) with the compound having an alcoholic hydroxyl group selected from (1) to (3) in the presence of the phospholipase DM at a temperature of about 0° to about 90° C.

* * * * *

UNITED STATES PATENT AND TRADEMARK OFFICE
CERTIFICATE OF CORRECTION

PATENT NO. : 4,782,019
DATED : 11/1/88
INVENTOR(S) : YOSHITAKA KOKUSHO ET AL.

It is certified that error appears in the above-identified patent and that said Letters Patent is hereby corrected as shown below:

Claim 1, in line 2 of the claim, "reprsented" should
  read --represented--;
Claim 1, in line 51 of the claim, "form" should read --from--
Claim 1, in line 61 of the claim, "sphingophoispholipid-
  primary" should read --sphingophospholipid-primary--;
Claim 1, in line 63 of the claim, "sphingosphospholipid-
  secondary" should read --sphingophospholipid-secondary--;
Claim 1, in line 64 of the claim, "sphingopospholipid"
  should read --sphingophospholipid--.

Signed and Sealed this

Twenty-first Day of March, 1989

Attest:

DONALD J. QUIGG

Attesting Officer

Commissioner of Patents and Trademarks